United States Patent [19]

Bagshawe et al.

[11] Patent Number: 5,716,990
[45] Date of Patent: Feb. 10, 1998

[54] DRUG DELIVERY SYSTEMS

[75] Inventors: Kenneth D. Bagshawe, London; Michael Jarman, Sutton; Caroline Joy Springer, London, all of England

[73] Assignee: Cancer Research Campaign Technology Limited, London, United Kingdom

[21] Appl. No.: 709,740

[22] Filed: Sep. 9, 1996

Related U.S. Application Data

[62] Division of Ser. No. 401,449, Nov. 7, 1989.

[30] Foreign Application Priority Data

Mar. 9, 1987 [GB] United Kingdom ............... 8705477

[51] Int. Cl.$^6$ .................. A61K 31/255; C07C 309/06; C07C 231/02
[52] U.S. Cl. .......... 514/517; 514/562; 514/563; 558/44; 558/47; 558/52; 558/53; 558/54; 564/138
[58] Field of Search ............... 562/430, 455; 514/562, 563, 517; 558/44, 47, 52, 53, 54; 564/138

[56] References Cited

U.S. PATENT DOCUMENTS

| | | | |
|---|---|---|---|
| 2,631,164 | 5/1953 | Weisblat et al. | 562/430 |
| 4,185,111 | 1/1980 | Ducep et al. | 514/99 |
| 4,564,675 | 1/1986 | Kurabayashi et al. | 536/18.1 |
| 4,675,187 | 6/1987 | Konishi et al. | 424/117 |
| 4,762,707 | 8/1988 | Jansen et al. | 424/180.1 |
| 4,975,278 | 12/1990 | Senter et al. | 424/94.3 |

FOREIGN PATENT DOCUMENTS

| | | |
|---|---|---|
| 1216791 | 1/1987 | Canada . |
| 0142905 | 5/1985 | European Pat. Off. . |
| 187658 | 7/1986 | European Pat. Off. . |
| 287353 | 10/1988 | European Pat. Off. . |
| 2584294 | 1/1987 | France . |
| 87/03205 | 6/1987 | WIPO . |

OTHER PUBLICATIONS

A. R. Ahmed et al., Ccyclophosphamide (Cytoxan). A review on relevant pharmacology and clinical uses, J. Am. Acad. Dermatol., Dec. 1984, pp. 1115–1126.

K. D. Bagshawe, Third Gordon Hamilton–Fairley Memorial Lecture, "Tumour markers–Where do we go from here?", Br. J. Cancer, 48, pp. 167–175 (1983).

I. Hellström et al., "Monoclonal Mouse Antibodies Raised Against Human Lung Carcinoma", Cancer Research, 46, pp. 3917–3923 (Aug. 1986).

G. W. Philpott et al., "Affinity Cytotoxicity of Tumor Cells With Antibody–Glucose Oxidase Conjugates, Peroxidase, and Arspehnamine", Cancer Research, pp. 2159–2164 (Sep. 1974).

I. Hellström et al., "Monoclonal Antibodies to Two Determinants of Melanoma–Antigen p97 Act Synergistically in Complement–Dependent Cytotoxicity", The Journal of Immunology, 127(1), pp. 157–160 (Jul. 1981).

V. J. Stella et al., "Prodrugs: A Chemical Approach to Targeted Drug Delivery", Directed Drug Delivery, pp. 247–267 (1985).

T. Nishiyama et al., "Antineoplastic Effects in Rats of 5–Fluorocytosine in Combination with Cytosine Deaminase Capsules", Cancer Research, 45, pp. 1753–1761 (Apr., 1985).

D. E. V. Wilman, "Prodrugs in Cancer Chemotherapy", Biochemical Society Transactions, 14, pp. 375–382, (615th Meeting, Belfast 1986).

P. J. O'Dwyer et al., The New England Journal of Medicine, 312, pp. 692–700 (Mar. 14, 1985).

A. P. Albino et al., "Heterogeneity in Surface Antigen and Glycoprotein Expression of Cell Lines Derived from Different Melanoma Metastases of the Same Patient", J. Exp. Med., 154, pp. 1764–1778 (Dec. 1981).

R. Amon et al., "In Vitro and In Vivo Efficacy of Conjugates of Daunomycin with Anti–Tumor Antibodies", Immunological Rev., 62, pp. 5–27 (1982).

K. D. Bagshawe, "Antibody Directed Enzymes Revive Anti–Cancer Prodrugs Concept", Br. J. Cancer, 56, pp. 531–532 (Nov. 1987).

K. D. Bagshawe, "A Novel Approach to Prodrug Activation Using a Monoclonal Antibody Conjugated to Carboxypeptidase G2", from the Third International Conference on Monoclonal Antibody Immunoconjugates for Cancer, Abstract #43, p. 70 (San Diego, Feb. 4–6, 1988).

R. W. Baldwin et al., "Design and Therapeutic Evaluation of Monoclonal Antibody 791T/36–Methotrexate Conjugates", Monoclonal Antibodies and Cancer Therapy, pp. 215–231 (1985).

R. W. Baldwin et al., Monoclonal Antibodies in Cancer Treatment, Lancet, pp. 503–605 (Mar. 15, 1986).

R. W. Baldwin et al., "Monoclonal Antibody Drug Conjugates for Cancer Therapy" Monoclonal Antibodies in Cancer: Advances in Diagnosis and Treatment, pp. 215–257 (1986).

(List continued on next page.)

Primary Examiner—Shailendra Kumar
Attorney, Agent, or Firm—Cushman Darby & Cushman Intellectual Property Group of Pillsbury Madison & Sutro, LLP

[57] ABSTRACT

Nitrogen mustard pro-drugs of the formula

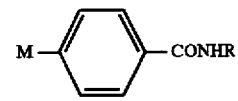

are disclosed where R is the residue of an α-amino acid $RNH_2$ and M is a disubstituted amino "mustard" group, useful in antibody directed enzyme pro-drug therapy in the treatment of cancer.

6 Claims, 3 Drawing Sheets

OTHER PUBLICATIONS

J. P. Brown et al., "Structural Characterization of Human Melanoma–Associated Antigen p97 with Monoclonal Antibodies", J. Immunology, 127(2) pp. 539–546 (Aug., 1981).

E. A. Clark et al., "Role of the Bp35 Cell Surface Polypeptide in Human B–Cell Activation", Proc.Natl. Acad.Sci., 82, pp. 1766–1770 (Mar. 1985).

S. T. Crook et al., (eds) Anthracyclines: Current Status and New Developments, Academic Press, cover pages and table of contents, (New York, 1980).

R. A. DeWeger et al., "Eradication of Murine Lymphoma and Melanoma Cells by Chlorambucil–Antibody Complexes", Immunological Rev., 62, pp. 29–45 (1982).

M. J. Embelton et al., "Antibody Targeting of Anti–Cancer Agents", Monoclonal Antibodies for Cancer Detection and Therapy, pp. 321–322 (1985).

M. J. Embelton et al., "Targeting of Anti–Cancer Therapeutic Agents by Monoclonal Antibodies", Biochemical Society Transactions, 14, pp. 393–395 (615th Meeting, Belfast 1986).

N. Endo et al., "In Vitro Cycotoxicity of a Human Serum Albumin–Medicated Conjugate of Methotrexate with Anti–MM46 Monoclonal Antibody", Cancer Research, 47, pp.1076–1080 (Feb. 15, 1987).

I. Hellström et al., "Antitumor Effects of L6, an IgG2a Antibody that Reacts with Most Human Carcinomas", Pro.Natl.Acad.Sci.U.S.A., 83, pp. 7059–7063 (Sep. 1986).

I. Hellström et al., "Antibodies for Drug Delivery", Controlled Drug Delivery, (2nd Ed.) pp. 638–642 (1987).

P. L. Ipata et al., "Baker's Yeast Cytosine Deaminase. Some Enzymic Properties and Allosteric Inhibition by Nucleosides and Nucleotides", Biochemistry, 10(23) pp. 4270–4276 (1971).

T. Katsuragi et al., "Affinity Chromatography of Cytosine Deaminase from Excherichia coli with Immobilized Pyrimidine Compounds", Agric. Biol. Chem., 50(7), pp. 1713–1719 (1986).

J.M. Lambert et al., "Purified Immunotoxins That Are Reactive with Human Lymphoid Cells", J. Biol. Chemistry, 260(22), pp. 12035–12041 (1985).

R. W. Baldwin et al. (eds), pp. 53–64, Academic Press (1985).

R. B. McComb et al. (eds), Alkaline Phosphatase, Plenum Press, Chapters 4, 5, 6 and 11 (New York 1979).

R. G. Melton et al., "In Vivo Localization of Carboxypeptidase G2–Antibody Conjugates in Human Colon Carcinoma Xenografts", from the Third International Conference on Monoclonal Antibody Immunoconjugates for Cancer, Abstract #83, p. 110 (San Diego, Feb. 4–6, 1988).

S. Monfardini et al. (eds), Manual of Cancer Chemotherapy, Third Ed., UICC Technical Support Series, 56, Table of Contents, pp. 1–230 (Geneva 1981).

F. L. Moolten et al., "Antibodies Conjugated to Potent Cytotoxins as Specific Antitumor Agents", Immunological Rev., pp. 47–73 (1982).

C. W. Parker et al., "Enzymatic Activation and Trapping of Luminol–Substituted Peptides and Proteins. A Possible Means of Amplifying the Cytotoxicity of Anti–Tumor Antibodies", pro. Nat.Acad.Sci. USA, 72(1), pp. 338–342 (1975).

G. W. Philpott et al., "Selective Iodination and Cytotoxicity of Tumor Cells with an Antibody–Enzyme Conjugate", Surgery, 74(1), pp. 51–58 (1975).

G. W. Philpott et al., "Selective Cytotoxicity of Hapten–Substituted Cells with an Antibody—Enzyme Conjugate", The Journal of Immunology, 111(3), pp. 921–929 (1973).

M. J. Robins et al., "Nucleic Acid Related Compounds. 16. Direct Fluorination of Uracil Nucleotides Using Trifluoromethyl Hypofluorite", Can. J. Chem., 53, pp. 1302–1306 (1975).

G. F. Rowland et al., "Drug Localisation and Growth Inhibition Studies of Vindesine–Monoclonal Anti–CEA Conjugates in a Human Tumour Xenograft", Cancer Immunol Immunother. 21, pp. 183–187 (1986).

F. Searle et al., "Antibody Carboxypeptidase G2 Conjugates as Anti–Tumor Agent", Tumor Biology, 6(4), p. 355 (1985).

F. Searle et al., "Carboxypeptidase G2 Conjugates with Localizing Anti–Tumour Antibodies: Potential Therapeutic Agents", Tumor Biology, 7(4), p. 320 (1986).

F. Searle et al., "The Potential of Carboxypeptidase G2 Antibody Conjugates as Anti–Tumour Agents. I. Preparation of Antihuman Chorionic Gonadotrophin–Carobyxpeptidase G2 and Cytotoxicity Against JAR Choriocarcinoma Cells In Vitro", Br. J. Cancer, 53, pp. 377–384 (1986).

W. T. Shearer et al., "Cytotoxicity with Antibody–Glucose Oxidase Conjugates Specific for a Human Colonic Cancer and Carcinoembryonic Antigen", Int. J. Cancer, 14, pp. 539–547 (1974).

V. J. Stella et al., "Prodrugs Do They Have Advantages in Clinical Practice?", Drugs, 29, pp. 455–473 (1985).

W. A. Thomas, "Prodrugs", Biochemical Society Transactions, 14, pp. 383–387, (615th Meeting, Belfast 1986).

P. E. Thorpe et al., "The Preparation and Cytotoxic Properties of Antibody–Toxin Conjugates", Immunological Rev., 62, pp. 119–158 (1982).

P. E. Thorpe, "Antibody Carriers of Cytotoxic Agents in Cancer Therapy: A Review", Monoclonal Antibodies '84 Biological and Clinical Applications, pp. 475–506 (1985).

E. S. Vitetta et al., "Redesigning Nature's Posions to Create Anti–Tumor Reagents", Science, 238, pp. 1098–1104 (1987).

M. Y. Yeh et al., "Cell Surface Antigens of Human Melanoma Identified by Monoclonal Antibody", Proc.Natl.Acad.Sci (USA, 76(6), pp. 2927–2931 (1979).

M. Y. Yeh et al., "Clonal Variation in Expression of a Human Melanoma Antigen Defined by a Monoclonal Antibody", J. Immunol. 126(4), pp. 1312–1317 (1981).

P. J. Fraker et al., "Protein and Cell Membrane Iodinations with a Sparingly Soluble Chloroamide 1,3,4,6–Tetrachloro–31,6a–Diphenylglycolunil", Biochem. Biophysical Research Comm., 80(4), pp. 849–857 (Feb. 1978).

J. P. Mach et al., "Improvement of Colon Carcinoma Imaging: From Polyclonal Anti–CEA Antibodies and Static Photoscanning to Monoclonal Fab Fragments and ECT", Monoclonal Antibodies for Cancer Detection and Therapy, pp. 53–64 (1985).

K. Ohkawa et al. "Selective in Vitro and In Vivo Growth Inhibition Against Human Yok Sac Tumor Cell Lines by Purified Antibody Against Human α–Fetoprotein Conjugated with Mitomycin C via Human Serum Albumin", Cancer Immunol. Immunother, 23, pp. 81–86 (1986).

1a
24 hrs 1b
72 hrs

FIG. 2a
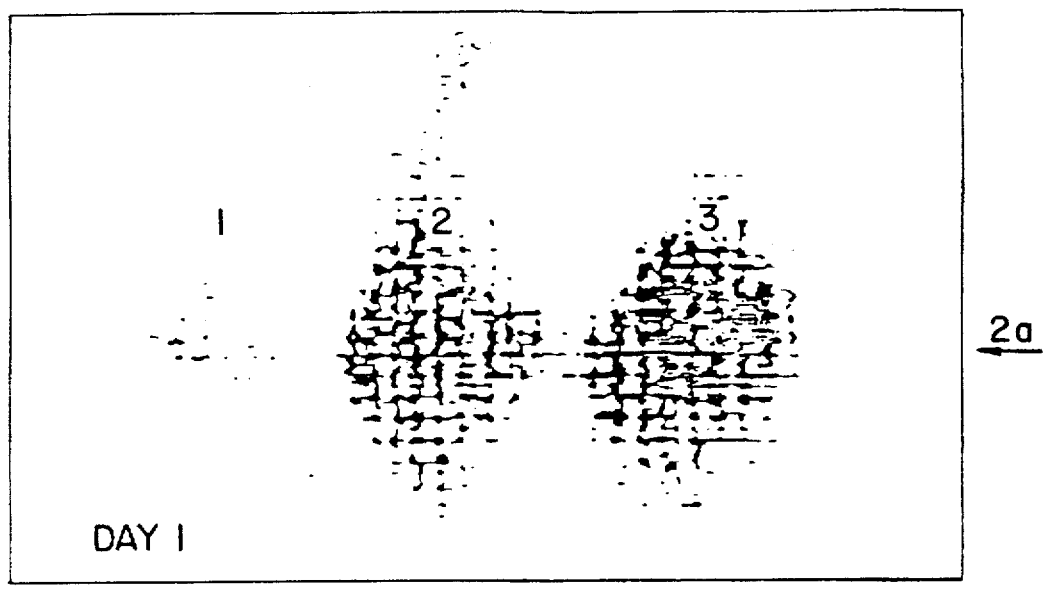
DAY 1
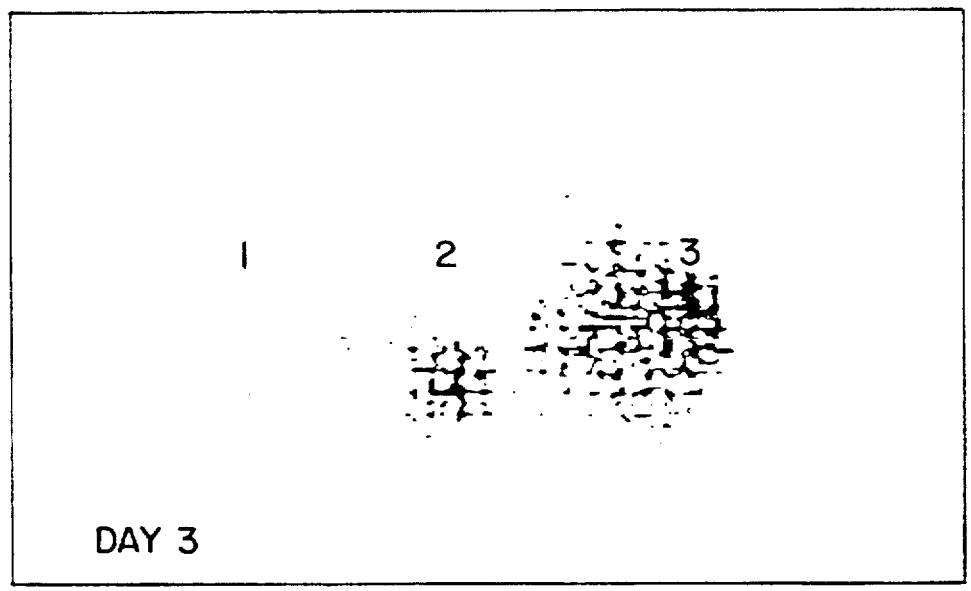
DAY 3
FIG. 2b

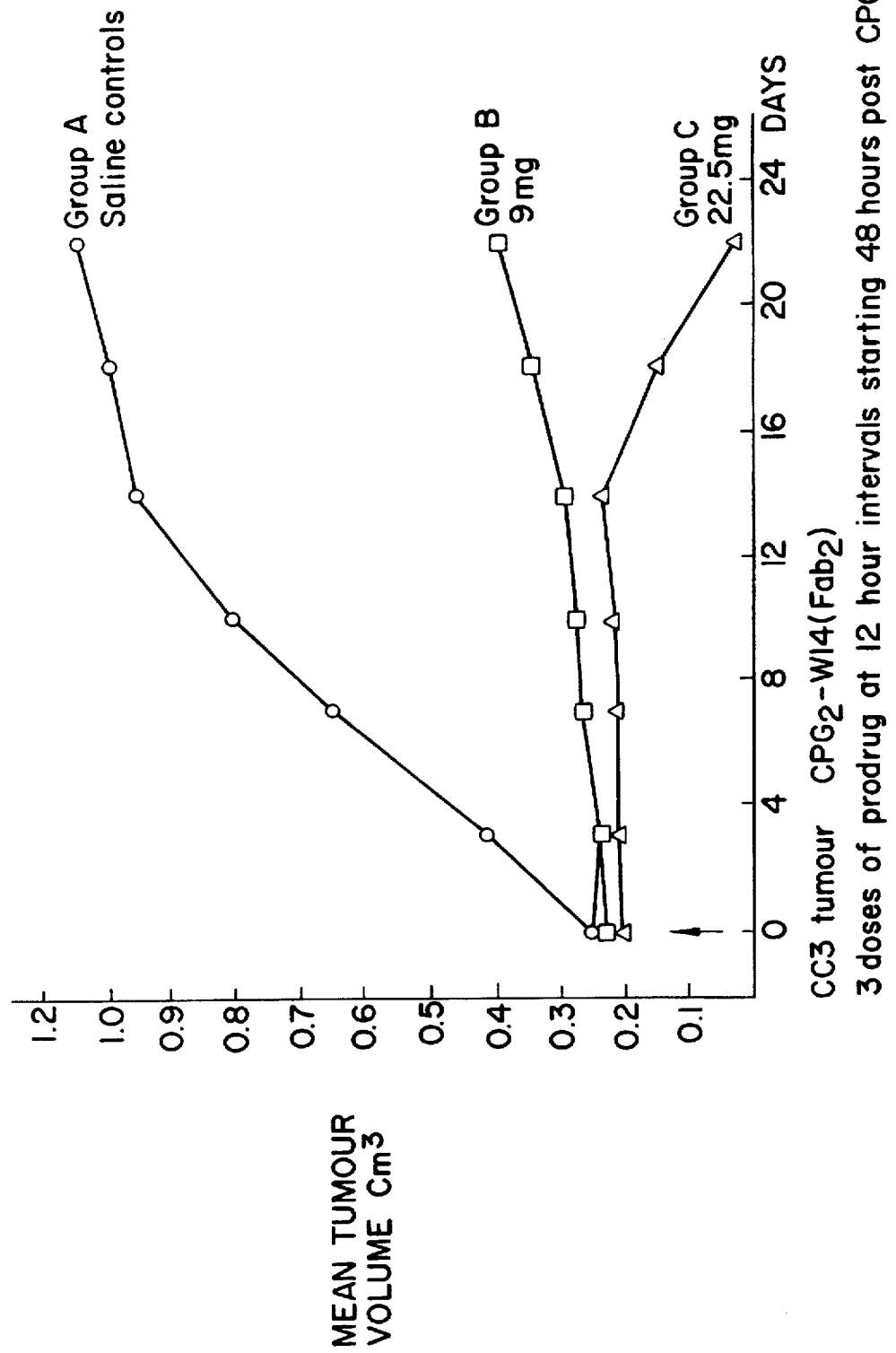

DRUG DELIVERY SYSTEMS

This is a division of application Ser. No. 07/401,449, filed Nov. 7, 1989.

This invention relates to drug delivery systems and is particularly concerned with systems involving interaction between pro-drugs and targetted triggers for the pro-drug.

BACKGROUND OF THE INVENTION

The pharmacological action of drugs used in the treatment of disease is largely determined by differences between cell types in the body and their anatomical location. It is advantageous to have the action of some drugs concentrated in certain tissues. Drugs have been developed which, by virtue of affinities for certain molecular groups have a modified pattern of retention within the body. Attempts to develop drugs which are selectively retained in certain tissues such as cancers have however proved difficult to achieve because of lack of specific molecular configurations in those tissues apart from the various cancer-associated antigens.

One of the main problems in the attack on human cancer is that of selectivity. Most of the drugs which are used are cytotoxic to normal tissues as well as to cancer.

Attempts have been made to improve the treatment of cancer by coupling anti-cancer drugs or radionuclides to antibodies or antibody fragments which have some degree of specificity for cancer associated antigens. The relatively large size of these antibody conjugates results in their slow diffusion through body spaces and into tumours. The conjugates are retained to a greater extent where the antigen is in a higher concentration than elsewhere. Maximum discrimination in distribution between tumour and non-tumour sites is therefore obtained only many hours or days after administration. At this time the concentration of the antibody drug complex has fallen to a relatively low level both in non-tumour and in tumour tissue. The effectiveness of therapy depends, in part, on the relative concentration of the active agent in the tumour and non-tumour tissues and the period of time for which effective concentration is maintained (often referred to as 'Areas under the Curve' AUC). The slow localisation of antibody drug complexes results in time x concentration values which are unfavourable for therapeutic purposes. Although 2 to 10% of an antibody dose can be demonstrated to localise in tumour target in mice the corresponding figure in man is nearer to 0.1%. There have been attempts in the past to develop anti-cancer drugs which would be in the form of pro-drugs and which would be activated by enzymes thought to be present in excess in certain tumours. Unfortunately these attempts have not succeeded because enzymes have not proved to be present in tumours either in sufficient quantity or with a sufficiently unique distribution to confer the necessary specificity of action. Enzymic activation of pro-drugs to an active form is however well established in principle and some of the widely used anti-cancer drugs, cyclophosphamide and iphosphamide are inactive as administered but converted by liver enzymes into active metabolites.

It has also been shown that an alkylating agent, aniline mustard, is rapidly inactivated by conjugation with a glucuronidase in the liver. The aniline mustard-glucuronide can be converted back into an active form by a glucuronidase. Unfortunately, such an enzyme occurs in sufficient amount only in one type of cancer and that occurs only in experimental mice.

A further example is the release of the alkylating agent phenylene diamine mustard from the peptidyl pro-drug valine-leucine-lysine-phenylene diamine mustard by plasmin. Plasmin is generated by the action of plasminogen activators on plasminogen.

SUMMARY OF THE INVENTION

We have recently shown that it is possible to conjugate an antibody or antibody fragment with an enzyme and that the resulting conjugate retains its antibody activity and its enzyme activity. We have now been able to develop this system further so as to provide for the selective delivery and release of a cytotoxic compound at a preselected site in active form.

In its broadest aspect, the present invention provides a two-component system designed for use in association with one another comprising:
(1) a first component that is an antibody fragment capable of binding with a tumour-associated antigen, the antibody fragment being bound to an enzyme capable of converting cytotoxic pro-drug into a cytotoxic drug.
(2) A second component that is a cytotoxic pro-drug convertible to the cytotoxic drug under the influence of the enzyme bound to the antibody fragment of (1) above.

Reference to the word "tumour" in this context and throughout the description is to be understood as referring to all forms of neoplastic cell growth, including leukemias.

BRIEF DESCRIPTION OF THE DRAWINGS

FIGS. 2a and 2b are gamma-camera images obtained 24 and 72 hours, respectively, after i.v. injection with MBS-linked conjugate and SPDP-linked conjugate of F(ab')$_2$:CFG2, Example 1(ii).

FIG. 3 is a graph of tumour volume as a function of time following administration of saline or pro-drug, from Example 5.

DETAILED DESCRIPTION OF THE INVENTION

Figure 1A:
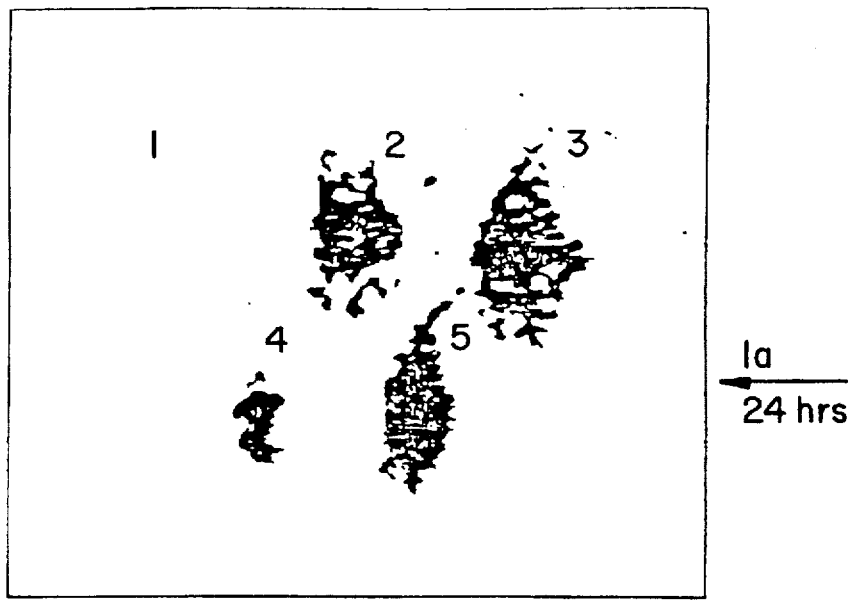
FIGS. 1a and 1b are gamma camera images obtained 24 and 72 hours, respectively, after i.v. injection with MBS-linked conjugate and SPDP-linked conjugate of W14A:CPG2, Example 1(i).

In accordance with the present invention, administration of the first component to a mammal bearing a tumour will result, provided that the first component is one that will recognise and bind to the tumour-associated antigen of the tumour, in the selective concentration of the first component in the region of the tumour. After a suitable period of time following the administration of the first component, a proportion of the antibody-enzyme complex will have located and specifically bound to tumour associated antigens.

By selection of an appropriate pro-drug, which will normally exhibit considerably less cytotoxicity than the drug itself, there will be a release of an effective amount of the cytotoxic compound where the antibody-enzyme is at a high concentration, that is, at the target site.

It will therefore be seen that a measure of selective therapy can be secured considerably in excess of the level if selectivity that has been obtainable by previous methods, particularly those where the cytotoxic compound is directly bonded to an antibody to a tumour-associated antigen or to those methods where reliance is placed upon the existence of endogenous enzymes in sufficient concentration to release the cytotoxic compound from the pro-drug.

The present invention is applicable, in principle, to the delivery of any type of cytotoxic compound in pro-drug form.

The characteristics required for each of the components in the system will now be described. The antigenic target or epitope to which the antibody is directed should ideally be a widely expressed component of the cancer cell membrane add one which is not secreted into body fluids. However, experience with immunoscintigraphy indicates that an antigen or epitope may be expressed to some extent by normal cells and that it may be shed by cancer cells or normal cells into body fluids without inhibiting the selective distribution of the antibody to cancer sites provided it is secreted more abundantly than the cancer cells.

Considerable work has already been carried out on antibodies and fragments thereof to tumour-associated antigens and antibodies are already readily available that recognise and bind, for example, to human chorionic gonadotrophin (hCG), alfa-fete-protein, carcinoembryonic antigen (CEA), and placental alkaline phosphatase (PLAP), prostate specific antigen, Ca-125 and human milk fat membrane proteins.

The antibody used in the preparation of the antibody-fragment-enzyme conjugate should have a high affinity for the target antigen or epitope but antibodies with a wide range of affinities have been successfully used in immunoscintigraphy. Antibody will generally be of the IgG class but other classes of immunoglobulin are not excluded. They may be polyclonal or more probably monoclonal and should be largely free of impurities. Antibody fragments may be prepared by standard procedures. The fragment of antibody used in the conjugate may possess one or more antigen binding sites and these may be conjugated to enzyme by alternative techniques which include chemical bonding or the production of a hybrid molecule by genetic engineering. Antibody fragments with two antigen binding sites which may have similar or different specificities and may be produced by standard procedures which remove the Fc fragment or they may be constructed by bonding together two fragments having only one antigen binding site each or by genetic engineering. The nature of the chemical bond or bridge between the two fragments should be such that it is not readily broken down in vivo and the bridge between the fragments in a constructed antibody may provide a suitable chemical structure for linkage to the enzyme. Since enzymes are also macromolecules a conjugate comprising intact antibody and enzyme is significantly larger than antibody alone and this may further delay distribution of the complex to cancer sites. Antibody fragments such as F(ab')$_2$ are smaller and not subject to non-specific binding due to Fc component and are therefore used as the antibody component in the antibody-enzyme conjugate although other antibody fragments, for example Fab$_1$, are not excluded.

A wide choice of suitable enzymes are available including hydrolases, amidases, sulphatases, lipases, glucuronidases and carboxypeptidases, phosphatases such as carboxypeptidase G2.

There are advantages in using a non-mammalian enzyme since if release of the cytotoxic drug from the pro-drug is only securable by the action of a non-mammalian enzyme, premature release of the cytotoxic drug from the pro-drug by endogenous enzymes is avoided.

The antibody fragment and the enzyme are normally linked together in a 1:1 ratio as this represents the simplest arrangement. However the present invention is not restricted to such 1:1 ratios.

In order to link chemically enzyme and antibody satisfactorily in a 1:1 ratio, a heterobifunctional linkage agent which is not labile in physiological conditions has to be employed. Carboxypeptidase G2, for example, and a suitable antibody can be linked together by enriching the antibody with thiol groups and treating the enzyme with a bifunctional agent capable of reacting with these thiol groups, e.g. the N-hydroxy-succinimide ester of iodoacetic acid NHIA (Rector et al), N-maleimidobenzoyl succinimide ester MBS (Sigma Ltd.), N-succinimidyl-3-(2-pyridyl-dithio)-propionate SPDP (Pharmacia Ltd). However, similar reactions generating a non-labile linkage can be envisaged with other published routes, or commercially available bifunctional agents: the compound produced need not be unique in the linkage except insofar that enzymatic and immunological activities must be maintained. The linkage methods can be applied to fragmented antibody (e.g. Fab'$_2$-anti-hCG) and to antibodies or fragmented antibodies directed towards other known tumour-associated antigens, such as those referred to above.

It will readily be appreciated that the principle of the present invention can be applied to the delivery of any cytotoxic drug that can be converted to a pro-drug for conversion back to the cytotoxic drug under the selective action of an enzyme. Thus, pro-drugs can be prepared from any of the various classes of anti-tumour compounds for example:

1. Alkylating agents (nitrogen mustards), for example cyclophosphamide, bisulphan, chlorambucil, nitroso ureas etc.
2. Intercalating agents, e.g. adriamycin and dactinomycin.
3. Spindle poisons, e.g. vinca alkaloids.
4. Anti-metabolites including anti-folates, anti-purines, anti-pyrimidines or hydroxyurea.

Our experiments have concentrated at this stage on the use of nitrogen mustards and one pro-drug of interest for use in the present invention is bis(2-chloroethyl)-amino benzoic acid where the carboxylic acid residue is protected by amidation with glutamic acid. The glutamyl side-chain can then be removed enzymatically, e.g. using carboxypeptidase, to release the nitrogen mustard.

Certain of the nitrogen mustards based on benzoic acid and substituted derivatives thereof, protected through amidation at the carboxy group e.g. with glutamic acid are new compounds and form a further aspect of the present invention.

The new compounds include those of the formula:

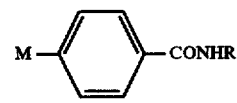

where M is a disubstituted amino "mustard" group and R is the residue of an α-amino acid RNH$_2$ and M is a

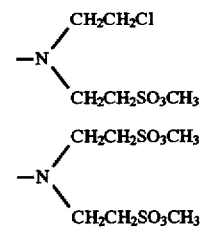

or

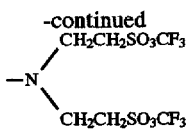

group.

The new compounds can be prepared either from the corresponding compound of the formula:

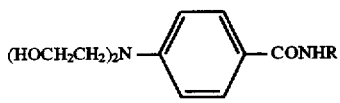

by reaction with a reagent that will replace the HO group by Cl, $CH_3SO_3$— or $CF_3.SO_3$— or by reacting the nitrogen mustard of formula:

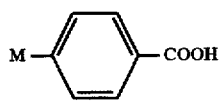

or a reactive carboxy derivative thereof with a carboxy protected amino acid $RNH_2$ and removing the carboxy protecting group.

For the purposes of illustration, these new compounds can be prepared, e.g. where the benzoic acid is to be substituted by a (2-chloroethyl)(2-chloroethyl)amino group from a compound of the formula I which is commercially available, the ethyl protected derivative of p-aminobenzoyl glutamic acid, by the following reactions:

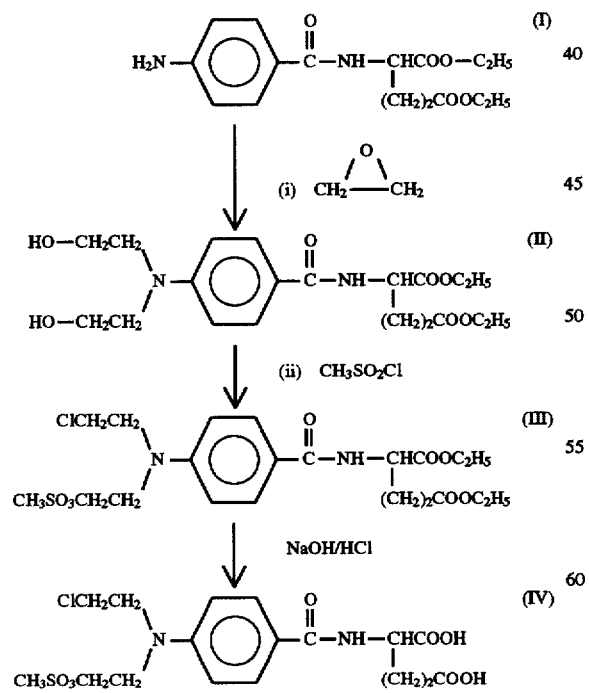

Other novel benzoic acid nitrogen mustard derivatives are suitable for demonstrating the efficacy the invention are:

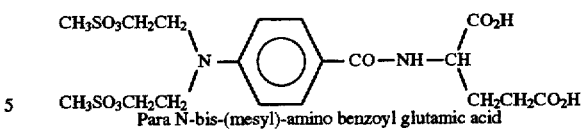
Para N-bis-(mesyl)-amino benzoyl glutamic acid

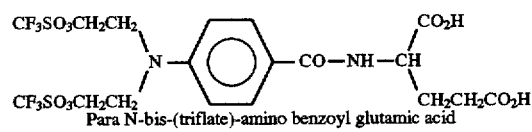
Para N-bis-(triflate)-amino benzoyl glutamic acid

Although the benzoic acid nitrogen mustards are useful for demonstrating the different aspects of this system experimentally, the difference in toxicity between the activated drug and pro-drug in cell culture experiments is only 5 to 10 fold, and this is likely to be reflected in the in vivo situation. Drugs for clinical use require this difference to be greater e.g. at least 100 times and preferably, 500–1000 times more toxic than the pro-drug. Examples of such pro-drugs are anthracyclines where the terminal amino group is derivatised as an amide with a D-amino acid, and nitrogen mustards based on p-phenylenediamine with halogen substituted alkanamido groups. For example, peptidyl pro-drugs of adriamycin and its analogues, derivatised at the essential amino group (i.e. R'):

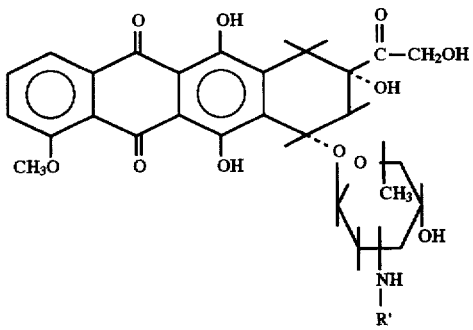

can be used as they can be subsequently released, as active drugs, by the above-mentioned or similar enzymes, to open the field to this range of anthracycline drugs.

Use may also be made of other antibody/enzyme conjugates with an appropriate pro-drug. As enzyme, use may be made of endoproteinase Lys-C from lysobacter enzymogenes (available from Boehringer Mannheim) which hydrolyses peptides specifically at the carboxyl group of lysyl residues. This enzyme has a molecular weight of 37,500 and pH optimum 7.7 making it a suitable enzyme to release a nitrogen mustard from a lysyl-rich-peptidyl prodrug. Clostripain (E C 3.4.22.8) from clostridium histolyticum is a highly specific endoprotease (available from Boehringer Mannheim) which cleaves peptides preferentially at the carboxyl site of L-arginine. Clostripain also cleaves arginine-proline peptide bonds which are not normally attacked by proteases. Its molecular weight of 50,000 and pH optimum, 7.6 make it a suitable candidate for conjugation with an antibody to release nitrogen in partnership with a mustard from an arginyl-prolyl-modified nitrogen mustard.

It is also possible to use an enzyme which releases a toxic nucleoside from its associated nucleotide.

The two-component system of the present invention can be used by sequential administration, the first component, the antibody fragment/enzyme conjugate being administered first followed by the pro-drug. In order to secure maximum concentration of the conjugate at the site of desired treatment, it is normally desirable to space apart administration of the two components by at least 4 hours. The exact regime will be influenced by various factors including the nature of the tumour to be targetted and the nature of the pro-drug, but usually there will be an adequate concentration of the conjugate at the site of desired treatment within 24 hours and frequently within 12 or even 8 hours so that the pro-drug can be administered at this time.

The two components will normally be administered parenterally and, in accordance with further aspects of the present invention, there is provided formulations of the conjugate and formulations of the pro-drug, the formulations being suitable for parenteral administration. Administration will normally be intravenous and such formulations are conveniently prepared in isotonic saline for injection.

For the purposes of demonstrating the efficacy of the present invention, we have worked with a model system using a monoclonal antibody W14A directed against human chorionic gonadotrophin (hCG), and F(ab')$_2$ fragments of the same antibody (2,4) and available from Damon Biotech Ltd., Kirkton Campus, Livingston, EH54, 7BT, Scotland.

In our experiments, we have used the enzyme carboxypeptidase G2, a folate degradating enzyme isolated from *Pseudomonas* (3), since this is an enzyme that is known to be capable of removing glutamate residues from folates, methotrexate and from nitrogen mustards derived from p-amino benzoic acid. The specific conjugates produced between carboxypeptidase G2 and the F(ab')$_2$ fragments of the monoclonal antibody (W14A) using the above-mentioned reagents retained enzymatic and immunological activity. The conjugate between carboxypeptidase G2 and the F(ab')$_2$ fragments of the monoclonal antibody (W14A) directed against hCG is a novel compound and forms a further part of this invention.

The pro-drug (Para-N-bis-(2-chloroethyl)aminobenzoyl glutamic acid) and its activated drug (benzoic acid mustard) used throughout the Examples was prepared by the general method described above for the production of the (2-chloroethyl)-(2-mesylethyl) compound but replacing the mesyl chloride by thionyl chloride. However, as mentioned above, because of the relatively low difference in toxicity between the drug and pro-drug, it is not anticipated that this particular pro-drug will be used in humans.

Example 1 is a comparison between a conjugate whole W14A or its F(ab')$_2$ fragment linked to CPG2.

The experiments of Example 1 show the superior properties of the fragment conjugate over the intact W14A conjugate, and the further Examples are concerned only with the use of the fragment conjugate.

EXAMPLE 1

Comparison between conjugates using intact antibody and F(ab')$_2$ conjugates

Intact W14A and F(ab')$_2$ fragment were conjugated with $^{131}$I- or $^{125}$I-labelled CPG2 using the coupling reagents N-maleimidobenzoyl succinimide ester (MBS), and N-succinimidyl-3-(2-pyridyldithio)-propionate (SPDP), which produce thioether (6) and disulphide bonds (7) respectively. The yields of the coupling reactions, with respect to antibody, were about 27% for SPDP, and 40% for MBS following separation from uncoupled antibody and CPG2 by gel filtration on Ultrogel AcA34 (8).

W14A: $^{131}$I-CPG2 conjugates were prepared using CPG2 of specific activity 960 uCi/mg. The specific radioactivity of MBS-linked W14A:CPG2 conjugate was 0.24 uCi/ug and SPDP linked W14A:CPG2 conjugate 0.21 uCi/ug.

F(ab')$_2$:$^{131}$I-CPG2 conjugates were prepared using CPG2 of specific activity 1048 uCi/mg. The specific radioactivity of MBS-linked F(ab')$_2$:CPG2 conjugate was 0.36 uCi/ug, and SPDP-linked F(ab')$_2$:CPG2 conjugate 0.34 uCi/Ug.

For imaging studies, intact W14A:$^{131}$I-CPG2 conjugates were injected i.v. or j.p. into nude rats bearing CC3 choriocarcinoma xenografts (9). F(ab')$_2$: $^{131}$I-CPG2 conjugates were administered by the i.v. route only. The animals were scanned using a Nuclear Enterprises LFOV gamma-camera.

Quantitative tissue distribution used groups of four nude mice bearing CC3 xenografts. The conjugates were prepared with $^{125}$I-labelled CPG2, and injected i.v., animals receiving approximately 2 uCi/45 ug each. Groups of animals were sacrificed at 24 hour intervals for the collection of tissue samples, which were dissolved in 6M KOH and counted in an LKB model 80,000 "Compugamma" counter.

RESULTS

Conjugates labelled only in the CPG2 moiety were used in order that any localising effect determined could be unambiguously attributed to localising of conjugate, rather than uncoupled antibody, which is difficult to eliminate entirely from conjugate preparations (8). The circulation half-life of native CPG2 is very short, about 3 hours in mice and 1 hour in rats, thus free enzyme would be quickly cleared. The enzyme does not appear to accumulate to a significant degree in any tissue (5).

(i) W14A:CPG2 Conjugates

Figure 1B:
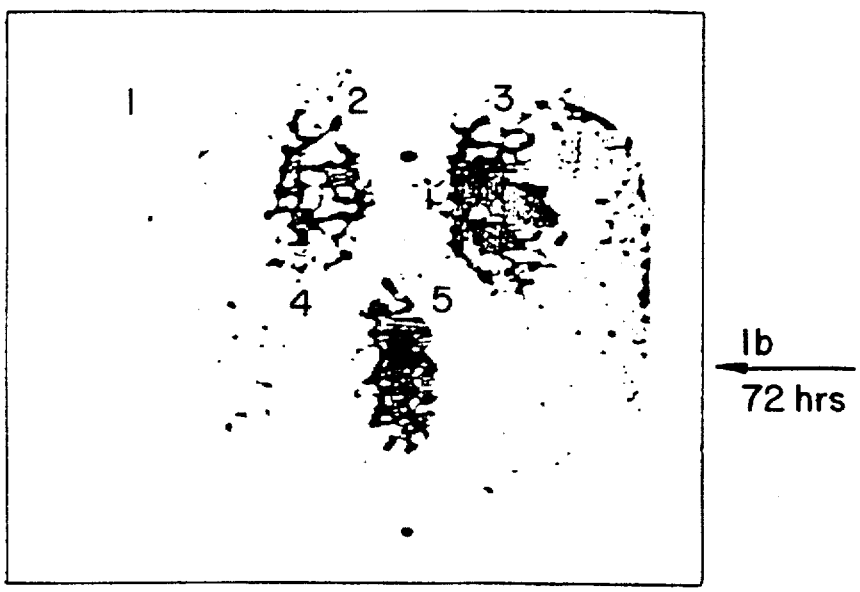

The gamma-camera images obtained after 24 and 48 hours are presented in FIGS. 1a and 1b respectively. In the cases of animals injected i.v. with MBS and SPDP linked conjugates the tumour site was clearly defined, confirming that localisation had occurred, but there was also substantial hepatic uptake. As expected, native enzyme was cleared rapidly from the circulation and no tumour or hepatic uptake was observed.

The SPDP-linked conjugates were cleared from the tumour more rapidly than MBS-linked material, suggesting that the disulphide linkage was less stable. Previous reports have suggested that disulphide bonds are labile in vivo (10, 11) and this method of linkage would appear to be unsuited to this application.

Animals injected i.p. with conjugate showed no tumour uptake, with SPDP-linked conjugate cleared by 48 hours and MBS-linked conjugate retained in the liver and blood pool. Pharmacokinetic studies (unpublished data) suggest that j.p. injection results in a slow release of conjugate into the circulation with peak levels only 30% of a comparable i.v. dose.

(ii) F(ab')$_2$:CPG2 Conjugates

The gamma-camera images obtained 24 and 72 hours after i.v. injection are presented in FIGS. 2a and 2b. MBS-linked conjugate showed a sharp tumour image with little or no uptake in the liver. SPDP-linked conjugate showed some uptake by the liver at 24 hours, but material was cleared by 72 hours. There was markedly less tumour uptake and these results reaffirmed the unsuitability of SPDP-linked conjugates for tumour imaging.

(iii) Quantitative Tissue Distribution of Antibody:Enzyme Conjugate

The tissue distribution of MBS-linked W14A and F(ab')$_2$:CPG2 conjugates in tumour, blood and liver are presented in Table 1.

TABLE 1

Major Tissue Uptake of W14A, and its F(ab')2 Fragment compared with W14A:CPG2 and F(ab')2: CPG2 Conjugates

|  | 24 hr | 48 hr | 72 hr |
|---|---|---|---|
| Tumour | | | |
| W14A | 1.48 | 0.94 | 0.85 |
| W14A:CPG2 | 0.23 | 0.21 | 0.22 |
| F(ab')2 | 0.76 | 0.39 | 0.29 |
| F(ab')2:CPG2 | 1.10 | 0.83 | 0.70 |
| Blood | | | |
| W14A | 2.01 | 1.09 | 0.63 |
| W14A:CPG2 | 0.87 | 0.41 | 0.34 |
| F(ab')2 | 0.83 | 0.27 | 0.10 |
| F(ab')2:CPG2 | 1.52 | 0.58 | 0.27 |
| Liver | | | |
| W14A | 0.98 | 0.59 | 0.33 |
| W14A:CPG2 | 0.27 | 0.11 | 0.09 |
| F(ab')2 | 0.33 | 0.13 | 0.05 |
| F(ab')2:CPG2 | 0.34 | 0.14 | 0.09 |

Values are calculated as percentage of the injected dose per gram of tissue and compared with intact W14A and F(ab')2 fragment controls. The results can be summarised:

The levels of F(ab')2:CPG2 in BLOOD were comparable to those found for W14A:CPG2 conjugate about 50% of the level of intact W14A about 3-fold higher than those of native F(ab')2 fragments.

The TUMOUR uptake of F(ab')2:CPG2 was comparable with that obtained with native W14A 3-fold higher than the levels attained with W14A:CPG2 conjugate or free F(ab')2.

The LIVER uptake of F(ab')2:CPG2 was lower than that of native W14A similar to levels attained with intact W14A:CPG2 conjugate or F(ab')2 fragments.

The level of uptake off F(ab')2 conjugates in lung, spleen, kidney, colon and muscle followed a similar pattern to that of liver, with levels being similar to native F(ab')2 fragments or W14A:CPG2 conjugate.

This demonstrates the advantages obtained by using F(ab')2:CPG2 conjugates rather than the W14A:CPG2 conjugate, as the ratio of the fragment conjugate in the tumour compared to the blood is 3 fold higher than for the W14A conjugate, though the background level of the fragment conjugate in other organs is similar to W14A:CPG2.

EXAMPLE 2

In vitro cytotoxicity of Pro-drug+Active Drug

This shows the toxicity relationship between a cytotoxic compound and its less toxic pro-drug.

The 50% growth inhibiting dose (ID50) for MAWI cells (colorectal cancer) in vitro ($5 \times 10^4$ cells/ml was 25 um with the active drug (benzoic acid mustard). The maximum inhibition that could be obtained with the pro-drug was 7% at a concentration of 400 um.

The ID50 for the pro-drug on MAWI cells with carboxypeptidase G2 (CPG2) present in the medium at a concentration of 6 units was 30 uM (i.e. very similar to that for the active drug).

For LS174 (colorectal cancer) cells the ID50 for active drug was 30 uM and also for pro-drug in the presence of CPG2 at 6 units ml. The pro-drug alone at 400 uM inhibited growth by 15% compared with untreated control cultures.

EXAMPLE 3

Distribution of Pro-drug and Active Drug in vivo, in plasma at 24 and 48 hours post antibody-enzyme conjugate Nude mice bearing human choriocarcinoma (CC3) tumour received 29 units of CPG2 conjugated to anti-HCG (W14Fab2) and after 24 or 48 hours received pro-drug (41 uM/kg). Control mice received the same dose of pro-drug but no CPG2-W14(Fab2) conjugate.

In the control mice the plasma concentration of pro-drug fell from 5 uM at 5 mins post injection to 0.8 uM at 3 hours; the active drug became detectable at 2 hours rising to 15 uM by 3 hours post injection. Mice receiving pro-drug and CPG2-W14(Fab2) had pro-drug levels of 2.8 uM at 5 mins post injection and 0.5 uM at 60 mins; active drug was detected at 200 uM at 5 mins falling to 2 uM at 3 hours.

Whether CPG2-W14(Fab2) was given 24 hours or 48 hours before there was at 5 mins after pro-drug administration, a 10-fold higher concentration of active drug in the plasma than there was even after 150 minutes in controls not receiving CPG2-W14(Fab2) showing that conversion of pro-drug to active drug occurred efficiently in vivo in the presence of the antibody enzyme conjugate.

EXAMPLE 4

Distribution of Pro-drug and Active Drug in vivo (Plasma and Tumour

Group 1 mice received pro-drug at 41 uM/kg and were bled, sacrificed and tissues removed at 5, 15, 30, 60, 120, 240 mins later.

Group 2 mice received active drug of equivalent molarity (41 uM/kg) otherwise as group 1.

Group 3 mice received 29 units of CPG2-W14(Fab2) conjugate 48 hours before pro-drug as per group 1.

Plasma:

In group 1 the peak concentration of pro-drug 30 uM fell to 2 uM at 120 mins. Active drug first became detectable at 120 min rising to 40 uM at 240 min.

In group 3 active drug concentration was 100 uM at 5 min, 150 uM at 30 min and 60 uM at 240 min.

Tumour:

In group 1 the tumour concentration of pro-drug at 5 min was 8 uM falling to 0.4 uM by 240 min; active drug was just detectable at 0.6 uM at 240 min.

In group 2 active drug concentrations were 35 uM at 30 min and 18 uM at 240 min.

In group 3 active drug concentrations varied around 20 uM throughout the study period.

Although the plasma concentration for group 3 is higher than tumour concentration the tumour values do not take account of drug covalently bound to DNA which would not be released by the extraction procedure used.

EXAMPLE 5

Therapeutic Experiment with CC3 Tumour

Nude mice bearing human choriocarcinoma tumour received saline (Group A) or a preparation of the pro-drug 9 mg (Group B) or 22.5 mg (Group C) at 48, 60 and 72 hours after receiving 100 units of CPG2-W14(Fab2). Tumour volumes were measured in 3 planes and their volumes calculated (FIG. 3). Group B mice showed a delay in the onset of tumour growth whilst the higher dose of drug produced complete regression of the tumour.

EXAMPLE 6 p-[(2-Mesylethyl)-(2-chloroethyl)-amino]benzoyl glutamide (Compound IV) is prepared by the reaction scheme illustrated above starting from p-bis(2-hydroxyethyl) amino-benzoyl glutamide ethyl ester, itself prepared by reaction of the p-aminobenzoyl glutamide ethyl ester with ethylene oxide by known methods. The bis-2-hydroxyethyl compound is refluxed in pyridine for 10 minutes at 80° C. using a 3:1 (molar) mesyl chloride/ dihydroxy compound to give a reaction product which includes 17–20% by weight of the desired diethyl ester of Compound IV. Mass spectrometry for purified diethyl ester indicates a molecular weight of 506. The diethyl ester protecting groups are then removed by treatment first with aqueous sodium hydroxide and the resulting disodium salt then treated with aqueous hydrochloric acid to give a product including Compound IV. Compound IV is isolated from the reaction product by high pressure liquid chromatography in 25% acetonitrile/water containing 1% acetic acid. Compound IV elutes at 306 minutes. The eluted product is shown by thin layer chromatography to be pure Compound IV. Compound IV was converted, for further identification purposes, into its dimethyl ester and mass spectrometry indicated a molecular weight of 478.

The corresponding bis-(2-mesylethyl) compound was prepared by a similar method in which the reflux with mesyl chloride was carried out at 2° C. for 20 minutes in pyridine using a 3:1 (mole) mesyl sulphate/dihydroxy compound.

The corresponding bis-(2-trifluoromesylethyl) compound can be prepared by a similar method in which the mesyl chloride is replaced by tetrabutylammoniumtrifluoromethane sulphonate, $(C_4H_9)_4\ N(CF_3SO_3)$.

REFERENCES

1. Begent, R. H. J. (1985), *Biochim. Biophys. Acta*, 780:151–166.

2. Searle, F., Adam, T. and Boden, J. A. (1986), *Cancer Immunol., Immunother.*, 21:205–208.

3. Sherwood, R .F., Melton, R. G., Alwan, S. M. and Hughes, P. (1985), *Eur. J. Biochem.*, 148:447–453.

4. Searle, F., Partridge, C. S., Kardana, A., Green, A. J., Buckley, R. G., Begent, R. H. J., and Rawlins, G. A. (1984), *Int. J. Cancer*, 33:429–434.

5. Melton, R. G. , Wiblin, C. N. , Baskerville, A., Foster, R. L. and Sherwood, R. F. (1986), *Biochem. Pharmacol.*, 35: in press.

6. Carlsson, J., Drevin, D. and Axen, R. (1978), *Biochem. J.*, 173:723–737.

7. Kitagawa, T. and Aikawa, T. (1976), *J. Biochem.*, 79:233–236.

8. Searle, F., Bier, C., Buckley, R. G., Newman, S., Pedley, R. B., Bagshawe, K. D., Melton, R. G. Alwan, S. M. and Sherwood, R. F. (1986), *Br. J. Cancer*, 53:377–384.

9. Searle, F., Boden, J. A., Lewis, J. C. M. and Bagshawe, K. D. (1981), *Br. J. Cancer*, 44:137–144.

10. Thorpe, P. E., Ross, W. C. J., Brown, A. N. F., Myers, C. D., Cumber, A. J., Foxwell, B. M. J and Forrester, J. A. (1984), *Eur. J. Biochem.*, 140:63–71.

11. Trowbridge, I. S. and Domingo, D. L. (1981), *Nature* (Lond.), 294:171–173.

We claim:
1. A nitrogen mustard pro-drug of the formula

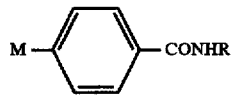

where R is a glutamic acid residue and M is a

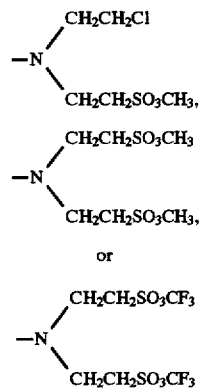

group.

2. A pro-drug according to claim 1 where R is a D-glutamic acid residue.

3. A process for preparing a compound as defined in claim 1 which comprises reacting a nitrogen mustard of formula

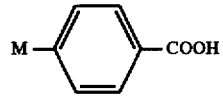

or a reactive carboxy derivative thereof with a carboxy protected amino acid R $NH_2$ and removing the carboxy protecting group.

4. A process for preparing a compound as defined in claim 1 which comprises reacting a compound of the formula:

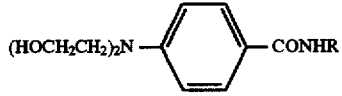

with a reagent capable of replacing the HO group by Cl, $CH_3SO_3$ or $CF_3SO_3$.

5. A pharmaceutical composition comprising a pro-drug according to claim 1 or 2 together with a pharmaceutically acceptable carrier or diluent.

6. A composition according to claim 5 suitable for intravenous administration.

* * * * *